United States Patent
Larsen et al.

(10) Patent No.: US 12,059,139 B2
(45) Date of Patent: Aug. 13, 2024

(54) DEVICE FOR MIXING A MEDICAL PASTE

(71) Applicant: Ferrosan Medical Devices A/S, Søborg (DK)

(72) Inventors: Kristian Larsen, Værløse (DK); Peter Lund Hammershøj, Brønshøj (DK)

(73) Assignee: Ferrosan Medical Devices A/S, Søborg (DK)

( * ) Notice: Subject to any disclaimer, the term of this patent is extended or adjusted under 35 U.S.C. 154(b) by 939 days.

(21) Appl. No.: 17/056,595

(22) PCT Filed: Jun. 26, 2019

(86) PCT No.: PCT/EP2019/067028
§ 371 (c)(1),
(2) Date: Nov. 18, 2020

(87) PCT Pub. No.: WO2020/002443
PCT Pub. Date: Jan. 2, 2020

(65) Prior Publication Data
US 2021/0219969 A1    Jul. 22, 2021

(30) Foreign Application Priority Data

Jun. 27, 2018   (EP) .................................. 18180036

(51) Int. Cl.
*A61B 17/00* (2006.01)
*A61J 1/20* (2006.01)

(52) U.S. Cl.
CPC ....... *A61B 17/00491* (2013.01); *A61J 1/2037* (2015.05); *A61J 1/2055* (2015.05);
(Continued)

(58) Field of Classification Search
CPC ..... A61B 17/00491; A61B 2017/00495; A61J 1/2037; A61J 1/2055; A61J 1/2062;
(Continued)

(56) References Cited

U.S. PATENT DOCUMENTS

| 2012/0029464 A1* | 2/2012 | Kragelund ............ A61J 1/2089 604/414 |
| 2012/0089088 A1* | 4/2012 | Foshee .................. A61J 1/2089 53/425 |
| 2013/0046270 A1 | 2/2013 | Foshee et al. |

(Continued)

FOREIGN PATENT DOCUMENTS

| DE | 10333384 A1 | 2/2005 |
| FR | 2903594 A1 | 1/2008 |

(Continued)

OTHER PUBLICATIONS

International Search Report, issued in international application No. PCT/EP2019/067028, entitled "Device for Mixing a Medical Paste", Date of Mailing: Sep. 26, 2019.

(Continued)

*Primary Examiner* — James D Ponton
(74) *Attorney, Agent, or Firm* — Hamilton, Brook, Smith & Reynolds, P.C.

(57) ABSTRACT

The invention regards a device for reconstituting a bioactive agent and forming a paste, the device comprising:—a container (2) containing the bioactive agent,—a first syringe (4) containing a liquid,—a second syringe (5) containing a paste forming material,—a connector element (6) configured for establishing sequential fluid connections between 1) the first syringe and the container, 2) the container and the second syringe, and 3) the first and second syringes, such that the liquid can be transferred from the first syringe to the container to reconstitute the bioactive agent, whereupon the reconstituted bioactive agent can be transferred from the container into the second syringe to form a paste, and the paste can be transferred to the first syringe.

20 Claims, 4 Drawing Sheets

(52) U.S. Cl.
CPC .......... *A61J 1/2062* (2015.05); *A61J 1/2089* (2013.01); *A61J 1/2096* (2013.01); *A61B 2017/00495* (2013.01)

(58) Field of Classification Search
CPC ........ A61J 1/2089; A61J 1/2096; A61J 1/065; A61J 1/2058; A61J 1/06; A61J 1/2048; A61M 2039/0027; A61M 5/1782; A61M 5/19

See application file for complete search history.

(56) References Cited

U.S. PATENT DOCUMENTS

| | | | |
|---|---|---|---|
| 2014/0251438 A1* | 9/2014 | Gettings | ................ A61L 27/10 137/897 |
| 2017/0136151 A1 | 5/2017 | Anderson et al. | |

FOREIGN PATENT DOCUMENTS

| | | |
|---|---|---|
| WO | 2006120461 A1 | 11/2006 |
| WO | 2007122209 A1 | 11/2007 |
| WO | 2007147741 A1 | 12/2007 |
| WO | 2009146088 A1 | 12/2009 |
| WO | 2010043685 A1 | 4/2010 |

OTHER PUBLICATIONS

Written Opinion, issued in international application No. PCT/EP2019/067028, entitled "Device for Mixing a Medical Paste", Date of Mailing: Sep. 26, 2019.

International Preliminary Report on Patentability, issued in PCT/EP2019/067028, entitled "Device for Mixing a Medical Paste", Date of Completion of Report: Apr. 2, 2020.

* cited by examiner

DEVICE FOR MIXING A MEDICAL PASTE

RELATED APPLICATIONS

This application is the U.S. National Stage of International Application No. PCT/EP2019/067028, filed Jun. 26, 2019, which designates the U.S., published in English, and claims priority under 35 U.S.C. § 119 or 365(c) to EP Application No. 18180036.8, filed Jun. 27, 2018. The entire teachings of the above applications are incorporated herein by reference.

FIELD OF INVENTION

The present invention relates to a device, a kit of parts, and a method for mixing a medical paste, such as a device and method for reconstituting a bioactive agent and for forming a flowable paste in a syringe.

BACKGROUND OF INVENTION

A paste may be precisely applied to a target site by use of a syringe. A syringe comprises a plunger, or piston, fitted to a barrel with an opening, where the barrel comprises the paste. By pushing or translating the syringe plunger along the barrel, the paste being in the form of an essentially non-compressible thick viscous composition, is discharged from the opening of the syringe barrel in a controlled manner. Thus, a paste may be delivered to a target site with high spatial precision and in a flexible dosage, by use of a syringe.

The delivery of a paste to a specific target site and in a precise amount, is essential for pastes, which are applied for medical purposes, such as for surgical applications. For example, haemostatic compositions for surgical applications are typically in the form of a paste.

An example of an effective surgical haemostat is a gelatine paste comprising a haemostatically effective amount of thrombin. Thrombin is a clotting agent, and may thus be used to control the bleeding at a haemorrhaging site. However, for the medical paste to be haemostatically efficient, it is essential that an effective concentration of the thrombin is present in the paste, and that the thrombin is uniformly distributed in the paste, and that the paste has a suitable viscosity and rheology for precise and fixed positioning.

Thus, to obtain an efficient medical paste, the step of manufacturing the paste with sufficient uniform distribution of the agents, as well as correct concentration of the bioactive agent, and correct ratios between the individual components, is essential.

The efficiency of the paste will depend on the paste storage time after preparation, since the paste consistency or rheology may degrade over time, and also the efficiency of the bioactive agent may degrade over time due to chemical instability. For most bioactive agents, the stable storage form is the dry state, and storage in a paste or other liquid states are not stable storage forms. The dry bioactive agent may be reconstituted to a liquid form by mixing with a liquid.

To ensure the quality and efficiency of the paste, medical pastes are typically prepared on-site and immediately prior to use. The on-site preparation demands high precision of the person preparing the paste, who typically is under time pressure during the surgical procedure. Thus, the step of preparing the paste involves a risk of incorrect concentration dosages of the bioactive agent, and insufficient mixing of the paste.

Mixing procedures and manipulations of different substances can be time consuming. In an Operation Room (OR) setting this time consumption may be critical when using a haemostatic paste for inhibiting bleedings as the surgeon will have to interrupt his procedure while waiting for the haemostat. Thus, the preparation time of the paste may cause increased blood loss and longer operating time of the surgical procedure.

Mixing substances from different containers may also potentially compromise the sterility of the haemostatic paste and can negatively affect the consistency of the haemostatic paste if not done correctly. A correct paste consistency is important for a satisfactory haemostatic effect.

Conventional haemostatic pastes are prepared by mechanical agitation and mixing of loose powder and liquid to provide uniformity of the composition. Only after the paste is formed may the paste be placed into a delivery means or applicator, e.g. a syringe, and applied to the wound.

This procedure has been improved by for example Surgiflo® Haemostatic Matrix (Ethicon) where one syringe (Syringe I) is preloaded with loose gelatine powder or a pre-wetted paste, and a second syringe (Syringe II) with liquid. When it is time to make a paste, Syringes I and II are connected via a luer lock and the solution in Syringe II is pushed into Syringe I. By passing the contents repeatedly back and forth between Syringes I and II, a homogeneous paste is formed.

Syringe II may in addition to the liquid comprise a bioactive agent in the form of thrombin. The bioactive agent may be reconstituted by mixing with the liquid immediately prior to use, such that a uniform mixture of bioactive agent and liquid is drawn into the originally empty syringe II. Conventional reconstitution includes using a syringe with a needle to withdraw the diluent from one separate vial and inject it into another separate vial containing the powdered thrombin, whereupon the latter vial is shaken or swirled to thoroughly mix the two constituents. The syringe with needle is then used to withdraw from this vial the desired amount of reconstituted thrombin solution which is then mixed with the contents of Syringe I to form a paste. Because separate containers are used, the person reconstituting the compound must be certain to mix the correct amounts such that a proper concentration of the mixture results.

Despite the advances in the field, there is a need for more simple, efficient, and reliable devices and methods for mixing a paste. Such devices and methods may minimize the risk of erroneously mixed pastes, and the associated waste of bioactive agent and inefficient treatment of the patient, as wells as reduce the preparation time of the paste.

SUMMARY OF INVENTION

The present invention provides a device, a kit of parts, and a method for a more simple, efficient, and reliable mixing of a medical paste. Advantageously, the medical paste is produced directly in a syringe. Further advantageously, the medical paste is produced from a kit of parts, where the parts may be simply attached to each other to form a self-containing system for sufficiently mixing the components of the paste, and where no manual measurements or weighing steps are needed. Advantageously, the components are preloaded in the kit of parts, such as syringes and container, in predefined amounts and ratios. Thus, measurements of components in correct amounts are avoided, and a predefined amount of paste is fast, easily, and conveniently produced.

Thus, for example the device, kit and method may be used for fast, easy, convenient, and reliable reconstitution of a bioactive agent, such as a lyophilized drug, with a liquid or diluent, and a paste forming material, usually in the form of a biocompatible polymer, to form a flowable haemostatic matrix for use in surgical procedures. Thus, the device and process may result in improved surgical procedures, including limited blood loss and lower operating time of the surgical procedures.

The present invention is surprisingly suitable for the incorporation of thrombin in haemostatic pastes, and facilitates that a haemostatic paste comprising thrombin may be generated in a few step operation. Such simple and fast method for preparing a haemostatic composition is highly valuable in the operating room where potential bleeding must be controlled in a fast and efficient manner.

A first aspect of the invention relates to a device for reconstituting a bioactive agent and forming a paste, the device comprising:
- a container (2) containing the bioactive agent,
- a first syringe (4) containing a liquid,
- a second syringe (5) containing a paste forming material,
- a connector element (6) configured for establishing sequential fluid connections between 1) the first syringe and the container, 2) the container and the second syringe, and 3) the first and second syringes, such that the liquid can be transferred from the first syringe to the container to reconstitute the bioactive agent, whereupon the reconstituted bioactive agent can be transferred from the container into the second syringe to form a paste, and the paste can be transferred to the first syringe.

A second aspect of the invention relates to a kit of parts for the device according to the first aspect, comprising a container containing a bioactive agent, a first syringe containing a liquid, a second syringe containing a paste forming material, and a connector element.

A third aspect of the invention relates to a method for reconstituting a bioactive agent and forming a paste, the method comprising:
a) providing a first syringe containing a liquid, a container containing a bioactive agent, a second syringe containing a paste forming material, and a connector element configured for establishing sequential fluid connections between 1) the first syringe and the container, 2) the container and the second syringe, and 3) the first and second syringes,
b) attaching the first syringe, the container, the second syringe to the connector element,
c) pushing the piston of the first syringe, whereby the liquid is transferred from the first syringe to the container to reconstitute the bioactive agent, and consecutively the reconstituted bioactive agent is transferred from the container into the second syringe to form a paste,
d) mixing the paste by alternately pushing the piston of the second syringe and the first syringe, such that the paste is transferred between the second and first syringes.

In a preferred embodiment, the mixing of step (d) of the third aspect is obtained by pushing the pistons at least 1 or 2 times.

In a preferred embodiment, the mixing of step (d) of the third aspect is obtained by pushing the pistons at least 6 times.

A fourth aspect of the invention relates to a method according to the third aspect, configured to be carried out using the device according to the first aspect or the kit according to the second aspect.

A fifth aspect of the invention relates to use of the device according to the first aspect or the kit according to the second aspect for the method according to the third aspect.

DESCRIPTION OF DRAWINGS

The invention will in the following be described in greater detail with reference to the accompanying drawings.

FIG. 2 shows an embodiment of the device according to the present disclosure, assembled from the kit of parts shown in FIG. 1A, and illustrating the sequential fluid flows. (A) shows an embodiment, where the connector element is adapted to provide a simultaneous fluid passageway between the first syringe and the container, and the container and the second syringe, such that when the piston of the first syringe is pushed to discharge the liquid, the forced liquid is transferred through the connector, and into the bioactive agent container forming a reconstituted bioactive agent, and the reconstituted bioactive agent is further forced into the second syringe forming a paste. (B) shows a subsequent embodiment, where the connector element is adapted to provide a fluid passageway between the first and second syringe, such that when the piston of the second syringe is pushed to discharge the paste, the forced paste is transferred through the connector element and into the first syringe. (C) shows a subsequent embodiment, where the piston of the first syringe is pushed to force the paste back into the second syringe.

DETAILED DESCRIPTION OF THE INVENTION

The invention is described below with the help of the accompanying figures. It would be appreciated by the people skilled in the art that the same feature or component of the device are referred with the same reference numeral in different figures. A list of the reference numbers can be found at the end of the detailed description section.

The present disclosure relates to a device, a kit, and a method for mixing a medical paste directly in a syringe. Subsequently, the medical paste may be discharged from the syringe, and delivered to a target site with high spatial precision and in a flexible dosage. An embodiment of a syringe containing a paste mixed according to the present disclosure is illustrated in FIG. 1B.

Figure 1:
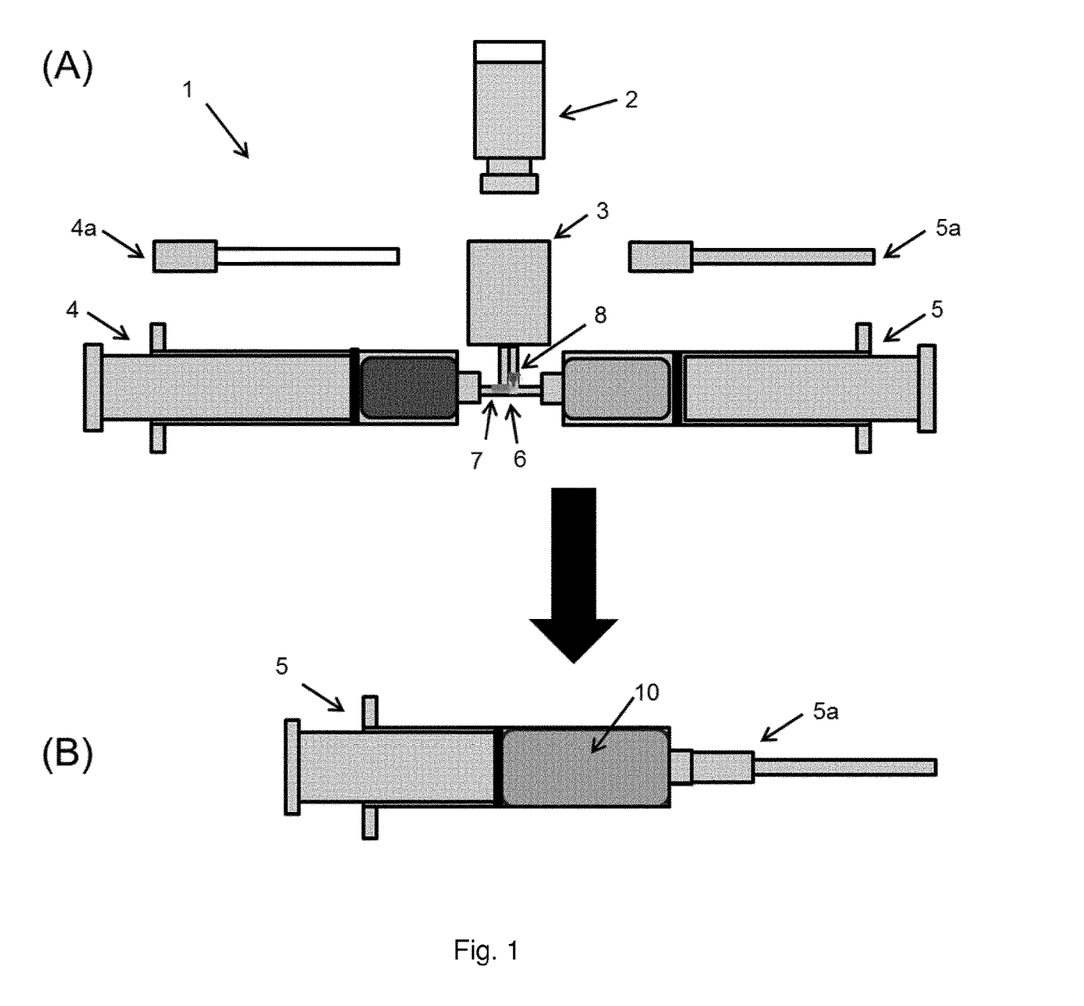
FIG. 1A shows an embodiment of the kit of parts according to the present disclosure for mixing a medical paste in a syringe.
FIG. 1B shows an embodiment of a ready to use syringe containing a paste mixed according to the present disclosure.

FIG. 1A shows an embodiment of the kit of parts for mixing the medical paste in the syringe embodied in FIG. 1B. The kit comprises a bioactive agent container 2, also known as a bioactive agent vial, a first syringe 4, a second syringe 5, and a connector element 6, where the bioactive agent container contains a bioactive agent, the first syringe is preloaded with a liquid, and the second syringe is preloaded with a paste forming material. Thus, the kit constitutes a predefined, self-containing system from which a medical paste may be formed, and where no manual measurements or weighing steps of any of the components of the paste are needed.

The preloaded syringes are needle free syringes as illustrated in FIG. 1A, where the possible corresponding syringe needles 4a and 4b are shown separately. The needle free syringes may be attached to the connector as illustrated in FIG. 1A, and simultaneously or subsequently the bioactive agent container may be attached to the connector. Optionally the bioactive agent container is attached to the connector at a container receiver 3 as illustrated in FIG. 1A.

By simply attaching the syringes and the bioactive agent container to the connector, the device 1 for mixing the medical paste is obtained. The mixing of the components is subsequently obtained by alternately pushing the piston of the first syringe, and the piston of the second syringe, whereby the contents of the container and syringes are sequentially forced and transferred through the connector in an order determined by the configuration of the connector.

Mixing Force

Pushing the pistons and the resulting transfer of the contents between the container and the syringes entail mixing of the components.

A preloaded syringe may be considered to define an amount of potential pressure energy. Upon pushing the plunger of the syringe, the pressure energy of the user is converted into kinetic energy for discharging the barrel content of the syringe. Thus, the preloaded syringe is a measure of a predefined amount of pressure energy.

Typically the syringe content is a fluid, such as a liquid, and the syringe fluid is discharged upon pushing the piston. When the discharged fluid is released into a container, the discharged fluid will be mixed with the materials of the container due to the kinetic energy and turbulent flow of the fluid. However, the degree of mixing, and thus the uniformity of the resulting mixture, will depend on the amount of kinetic energy, the viscosity of the discharged fluid, and the viscosity of the material in the container. The higher the viscosity, the more energy is needed for producing a uniform mixture.

If the discharged fluid is a liquid, and the container material is a fluid, a low amount of energy is needed for forming a uniform mixture between the two fluids. If on the other hand the the discharged fluid is a liquid and the second container material is a paste, more energy is needed for forming a uniform mixture between the fluid and the paste component. More drastically, if the discharged syringe content is a paste, and the container material is a paste, even more energy is needed for forming a uniform mixture between the two components.

The container material may also be a solid, such as particles of powder. In this case, the fluid solubility and/or the ability of the fluid to suspend the solid particles, in addition to the kinetic energy, will affect the ability to form a uniform mixture between the solid and the discharged fluid.

It was surprisingly found that sufficient reconstitution of a bioactive agent, and further sufficient mixing of the reconstituted agent to form a uniform paste may be obtained with the kit and device according to the present disclosure. Thus, the device provides a self-containing system for sufficiently mixing the components of the paste, where no manual measurements or weighing steps are needed.

Connector Element

As described above, the mixing of the components is obtained by alternately pushing the piston of the first syringe, and the piston of the second syringe, whereby the contents of the container and syringes are sequentially forced and transferred through the connector in an order determined by the configuration of the connector.

The connector element is configured for establishing sequential fluid connections between 1) the first syringe and the container, 2) the container and the second syringe, and 3) the first and second syringes, such that the liquid can be transferred from the first syringe to the container to reconstitute the bioactive agent, whereupon the reconstituted agent can be transferred from the container into the second syringe to form a flowable paste, and the flowable paste can be transferred to the first syringe.

This sequential fluid flow facilitates a mixing procedure, where a predefined amount of pressure energy is used in the mixing process, at the same time as obtaining a sufficient uniformly mixed paste. Thus, the procedure is simple to use, and provides an optimized use of energy, thereby facilitating faster mixing and preparation time.

Figure 2:
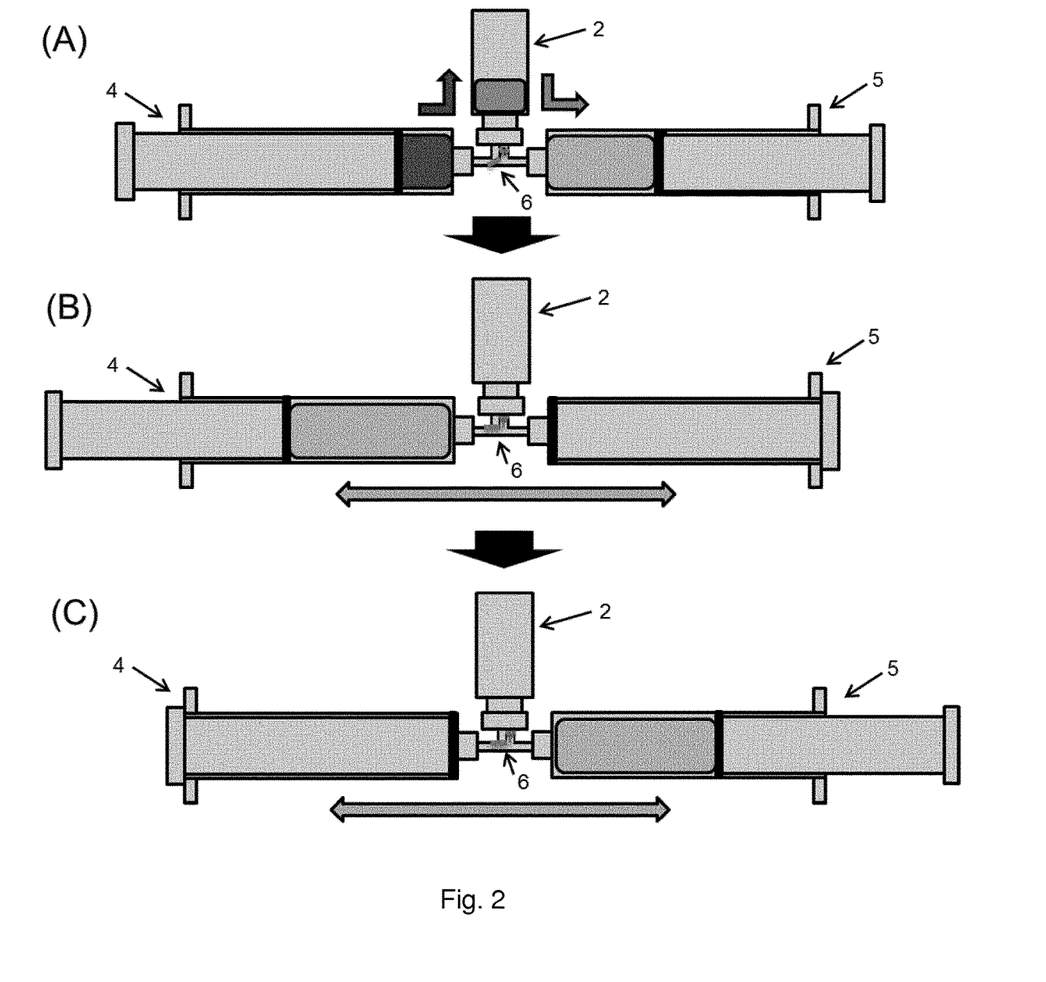

The sequential fluid flow is further illustrated in FIG. 2. FIG. 2A shows the device, assembled from the kit of parts shown in FIG. 1A, where the first syringe 4, the bioactive agent container 2, and the second syringe 5 has been attached to the connector element 6.

Following the assembly, the piston of the first syringe is pushed to discharge the liquid. Due to the configuration of the connector, the liquid is forced from the first syringe, through the connector, and transferred to the bioactive agent container, where it mixes with the bioactive agent. Due to the kinetic energy and turbulent flow of the liquid, the bioactive agent is essentially instantly uniformly mixed with the liquid, thereby forming a reconstituted bioactive agent.

Due to the configuration of the connector element, the kinetic energy of the original fluid, as well as gravitational force, the reconstituted bioactive agent is further forced from the container to the second syringe. Since the process of reconstitution occurs essentially instantly, the connector is advantageously adapted for providing fluid passageway between the first syringe and the container, simultaneously with providing fluid passageway between the container and the second syringe.

Thus, the transfer of the liquid to the bioactive agent container, and further to the second syringe occurs spontaneously when pushing the piston of the first syringe. The term "spontaneous" is used to describe phenomena arising from internal forces or causes, which are independent of external agencies or stimuli and which happen within a short period of time, i.e. preferably within less than about 30 seconds, more preferred within less than about 20 seconds, even more preferred within less than about 10 seconds or within less than about 5 seconds, such as within less than about 3 seconds, for example less than about 2 seconds.

When the reconstituted bioactive agent is transferred to the second syringe, it mixes with the paste forming material to form a paste. Preferably, the kinetic energy of the reconstituted agent is sufficient to obtain a uniform mixture and a uniform paste spontaneously. However, due to the properties of the paste forming material, e.g. the viscosity and particle sizes, sufficient uniform mixing of the paste forming material and the reconstituted bioactive agent may not occur instantly. Thus, to obtain a paste with a uniform distribution of the bioactive agent within the paste, the paste may be further mixed.

The further mixing of the paste may be carried out by transferring the paste from the second syringe to the first syringe, as illustrated in FIG. 2B, and optionally further back to the second syringe, as illustrated in FIG. 2C. Advantageously, the paste is transferred a minimum number of times, to reduce the amount of pressure energy needed for obtaining a uniform mixture. However, the transferring of the paste back and forth between the syringes may be repeated any number of times to ensure sufficient mixing. It was surprisingly found that sufficient mixing of the paste may be obtained with a limited number of piston movements after the components are initially contacted in the second syringe, such as between 1-6 piston movements.

In an embodiment of the disclosure, the mixing of the paste is obtained by pushing the pistons at least 1-6 times, such as 1 or 2 times after the components are initially contacted in the second syringe.

In an embodiment of the disclosure, the mixing of step of the paste is obtained by pushing the pistons at least 6 times.

The transferring of the paste between the syringes is facilitated by the connector having a second configuration, providing a fluid passageway between the first and second syringe. Thus, after the reconstituted bioactive agent is transferred to the second syringe, the configuration of the connector is changed from the first configuration to the second configuration.

In an embodiment of the disclosure, the connector element is adapted to have a first configuration providing simultaneous fluid passageway between the first syringe and the container, and the container and the second syringe, and a second configuration providing a fluid passageway between the first and second syringe.

In an embodiment of the disclosure, the two configurations of the connector element is obtained by at least two valves 7, 8 placed in the connector element. A valve is a device that regulates, directs or controls the flow of a fluid (gases, liquids, fluidized solids, such as paste and slurries) by opening, closing, or partially obstructing various passageways. A valve may further be a one-way valve, meaning that the valve only allows the fluid to flow in one direction.

FIG. 3 shows an embodiment of the connector element 6 according to the present disclosure, where the operation of the valves during the sequential fluid flows is illustrated. The valves may form two arrangements, where (A) shows the first arrangement providing simultaneous fluid passageway between the first syringe 4 and the container 2, and the container and the second syringe 5, and (B)-(C) shows the second arrangement providing a fluid passageway between the first and second syringe.

In an embodiment of the disclosure, the connector element comprises at least two valves 7, 8 adapted to have a first arrangement providing simultaneous fluid passageway between the first syringe and the container, and the container and the second syringe, and a second arrangement providing a fluid passageway between the first and second syringe.

To ensure efficient reconstitution and mixing, the sequential fluid flows are necessary. This requires that the fluid passageway between the first and second syringe is blocked, when the fluid passageway between the first syringe, container, and second syringe is open. Similarly, it requires that the fluid passageway between the first syringe, container, and second syringe is blocked, when the fluid passageway between the first and second syringe is open.

To reduce the complexity of the device and the number of parts, at least one of the valves advantageously have a dual function. This means that the valve has an “open” and “closed” position, where it in the open position provides fluid passageway in one direction, and simultaneously block/close fluid passageway in a second direction, and in the closed position provides fluid passageway in the second direction, simultaneously block/close fluid passageway in the first direction. Thus, the valve essentially functions as a flow direction controller with two set points.

FIGS. 3A-C show an embodiment, where the first valve 7 is exemplified as a flap valve adapted as a flow direction controller with two set points. At the first set point (A), the valve is open to direct fluid passageway between the first syringe and the container, and blocks the fluid passageway between the first and second syringe. At the second set point (A,B), the valve is open to direct fluid passageway between the first and second syringe, and blocks the fluid passageway between the first syringe and the container.

In an embodiment of the disclosure, at least the first valve is adapted as a flow direction controller with two set points, such that it either provides a direct fluid passageway between the first syringe and the container, or a direct fluid passageway between first and second syringe.

To reduce the complexity of the device, and further make it self-contained, it is advantageous that the configuration of the connector changes automatically, when the reconstituted bioactive agent has been transferred to the second syringe.

The exemplified flap valve may be pivotable mounted, such that the first set point is adopted due to gravity, when the connector is placed in a certain orientation. For example as illustrated in FIG. 3A, the connector element may have the shape of an inverse T, such that a part of the connector may be horizontally oriented, while the other part is vertically oriented, perpendicularly pointing upwards away from the horizontal part. In this orientation, the flap valve 7 of FIG. 3A may be pivotably pulled by gravity, and block the fluid passageway the horizontal part of the connector, i.e. the passageway between the first and second syringes. Thus, in FIG. 3A the first valve 7 is blocking the fluid passageway between the first and second syringes due to gravity.

The second valve may also operate in response to gravity. Thus, when the connector is kept in the orientation as shown in FIG. 3A, the second valve 8 is configured to be in an open position due to gravity, as illustrated in FIG. 3A.

Thus, by pushing the first syringe 4, the liquid from the first syringe is transferred to the container, and subsequently the reconstituted agent passes the open second valve 8, and goes into the second syringe to contact the paste forming material.

Subsequently, the paste of the second syringe may be transferred to the first syringe, by pushing the piston of the second syringe, as illustrated in FIG. 3B. Due to the high viscosity of the paste, the second valve 8 is pushed into a closed position, and the gravity force on the first valve 7 is counteracted, such that a fluid passageway between the first and second syringes is established, as illustrated in FIG. 3B.

This second set point configuration of the valves may be maintained upon any subsequent transfers of the paste between the first and second syringes, as illustrated in FIG. 3C.

Figure 3:
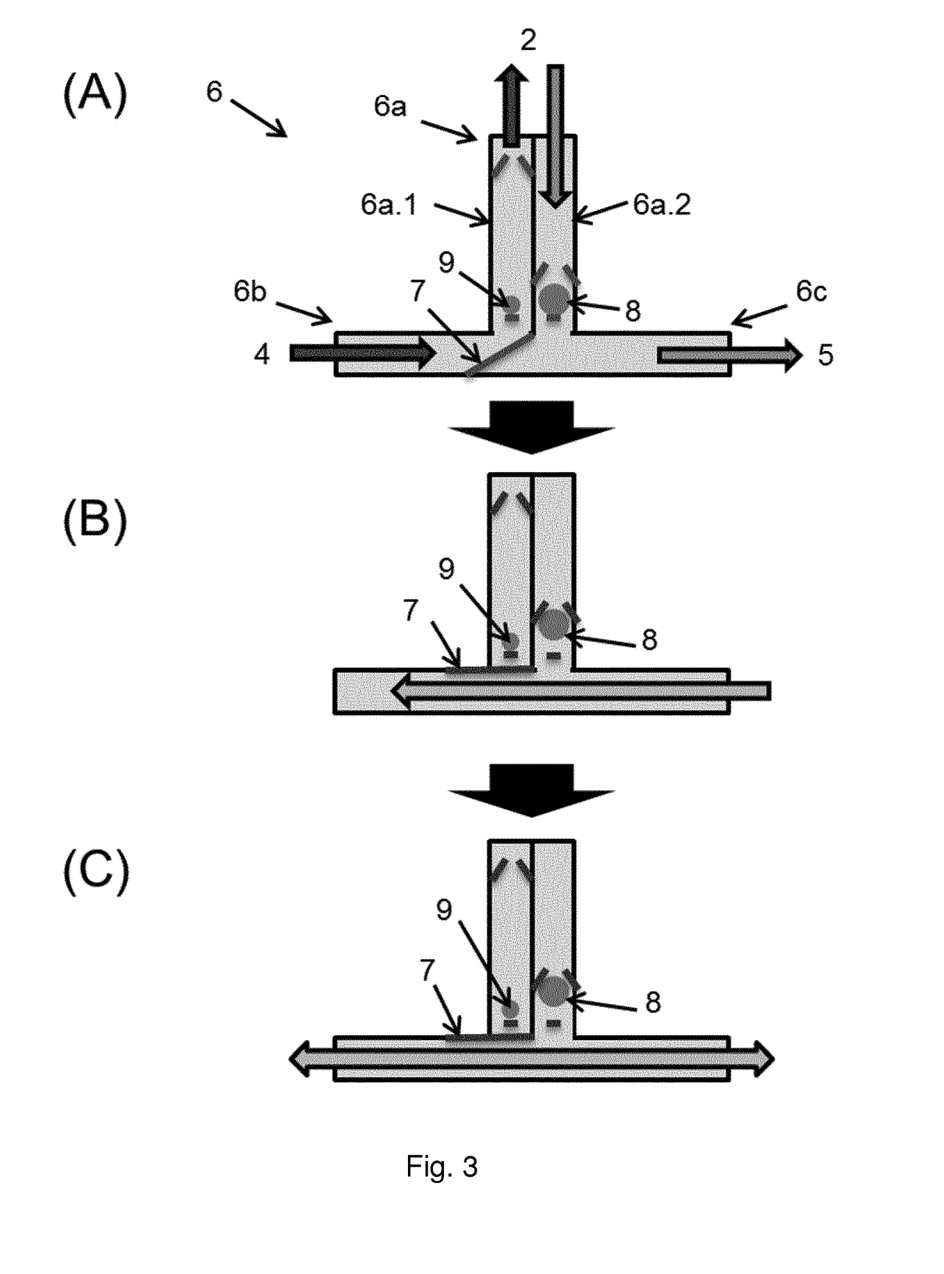
FIG. 3 shows an embodiment of the connector element 6 according to the present disclosure, where the operation of the valves 7, 8 during the sequential fluid flows is illustrated. The valves may form two arrangements, where (A) shows the first arrangement providing simultaneous fluid passageway between the first syringe 4 and the container 2, and the container and the second syringe 5, and (B)-(C) shows the second arrangement providing a fluid passageway between the first and second syringe. The first valve 7 is adapted as a flow direction controller with two set points.

FIG. 3 shows an embodiment of a connector element, where the valves are operating in response to gravity and the paste viscosity, such that the configuration of the connector changes automatically, when the reconstituted bioactive agent has been transferred to the second syringe.

A connector element, where the configuration changes automatically when the reconstituted bioactive agent has been transferred to the second syringe, may be obtained in different ways. For example, at least one of the valves may operating in response to gravity, liquid pressure, and/or magnetic forces.

Figure 4:
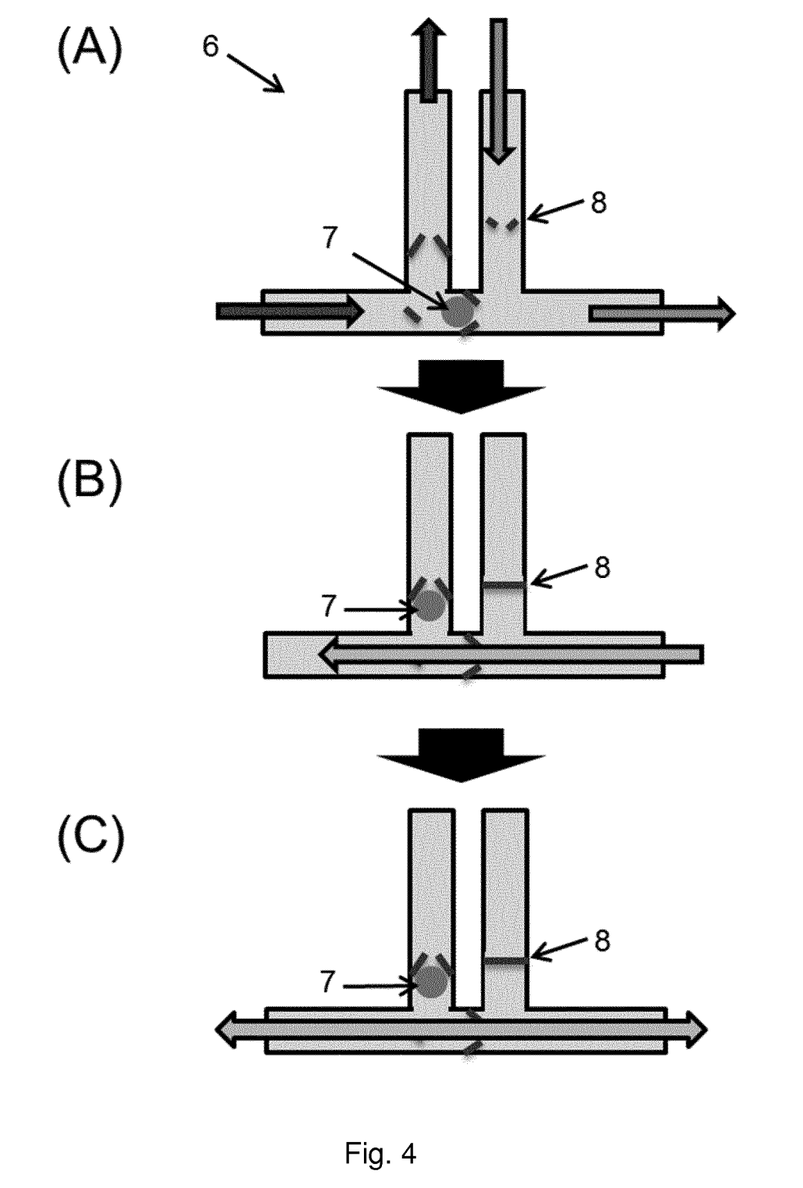
FIG. 4 shows another embodiment of the connector element 6 according to the present disclosure, where the operation of the valves 7, 8 during the sequential fluid flows is illustrated. The valves may form two arrangements, where (A) shows the first arrangement providing simultaneous fluid passageway between the first syringe 4 and the container 2, and the container and the second syringe 5, and (B)-(C) shows the second arrangement providing a fluid passageway between the first and second syringe. The first valve 7 is adapted as a flow direction controller with two set points.

FIG. 4 shows an embodiment of a connector element, where the first valve 7 is operating in response to mainly a liquid pressure. When the liquid from the first syringe is transferred to the connector, the liquid pressure pushes the first valve into the first set point, as illustrated in FIG. 4A. The first set point blocks the fluid passageway between the first and second syringes, and facilitates that the liquid flows into the container. As the reconstituted agent flows further from the container, the liquid pressure pushes the second valve 8 into an open position, as illustrated in FIG. 4A. Thus, the reconstituted bioactive agent passes the open second valve 8, and goes into the second syringe to contact the paste forming material.

Subsequently, the paste of the second syringe may be transferred to the first syringe, by pushing the piston of the second syringe, as illustrated in FIG. 4B. Due to the high viscosity of the paste, the second valve 8 is pushed into a closed position, and the first valve 7 is pushed into the second set point, where a fluid passageway between the first and second syringes is established, as illustrated in FIG. 4B. This second set point configuration of the valves may be maintained upon any subsequent transfers of the paste between the first and second syringes, as illustrated in FIG. 4C.

To reduce the complexity of the device, and further make it self-contained, it is advantageous that the valves are mechanically simple, and may be operated purely by gravity and/or liquid pressure.

In an embodiment of the disclosure, one or more of the valves are adapted to be controlled by a liquid pressure and/or gravity.

To ensure efficient reconstitution and mixing, the sequential fluid flows are necessary. Thus, to reduce the risk of erroneous fluid flows, it is advantageous that the device is adapted for providing only a unidirectional fluid flow from the first syringe to the container, and from the container to the second syringe, when the first valve is in the first set point, and adapted for providing a bidirectional fluid flow from the second syringe to the first syringe and vice versa, when the first valve is in the second set point. This may be ensured by use of one-way valves. An example of a one-way valve is a ball valve 8 as shown in FIG. 3.

In an embodiment of the disclosure, the device is adapted for providing a unidirectional fluid flow from the first syringe to the container, and from the container to the second syringe, when the first valve is in the first set point. In a further embodiment, the device is adapted for providing a bidirectional fluid flow from the second syringe to the first syringe and vice versa, when the first valve is in the second set point. In an embodiment of the disclosure, the first valve is a one-way valve. In a further embodiment, the second valve is a one-way valve.

The sequential fluid flow may further be obtained with a connector element having the shape of an inverse T (i.e. ⊥) as exemplified in FIGS. 3 and 4. The three sections of the connector 6a, 6b, 6c are then attached to respectively the container, the first syringe, and the second syringe as indicated in FIG. 3. The first section further comprises two lumens 6a.1, 6a.2, where the lumens may be adjacent as illustrated in FIG. 3, or separate as illustrated in FIG. 4.

In the embodiments, the first valve is configured for controlling flow of the first lumen 6a.1, and the second valve is configured for controlling the flow of the second lumen 6a.2. This may be obtained by placing the second valve in the second lumen, and placing the first valve in the first lumen, advantageously at the fluid inlet of the lumen as shown in FIGS. 3-4. Thus, the first lumen 6a.1 is configured for fluidly connecting the first syringe to the container, and the second lumen 6a.2 is configured for fluidly connecting the container to the second syringe, when first valve is in the first set point.

In an embodiment of the disclosure, the connector comprises a first section 6a for fluidly attaching the container, a second section 6b for fluidly attaching the first syringe, a third section 6c for fluidly attaching the second syringe. In a further embodiment, the first, second, and third sections of the connector form an inverse T-shape. In a further embodiment, the first section comprises two lumens 6a.1, 6a.2.

In a further embodiment, the first valve 7 is configured for controlling the flow of the first lumen 6a.1, and the second valve 8 is configured for controlling the flow of the second lumen 6a.2. In a further embodiment, the second valve is placed in the second lumen. In a further embodiment, the first valve is placed at a fluid inlet of the first lumen. In a further embodiment, the first lumen 6a.1 is configured for fluidly connecting the first syringe to the container, and the second lumen 6a.2 is configured for fluidly connecting the container to the second syringe, when first valve is in the first set point.

It is advantageous that the orientation of the connector is as illustrated in FIGS. 3-4, where the first section of the connector is oriented vertically and pointing upwards. This ensures that the bioactive agent is fully reconstituted and fully transferred to the second syringe, such that all the content of the bioactive container 2 is used. Thus, the orientation ensures efficient sequential fluid flows. Furthermore, in the case where the valves are controlled by gravity, the orientation may facilitate correct function of the valves and avoid improper use.

To ensure that the device is used in the upward orientation, a third valve 9 may be placed adjacent to the outlet of the first lumen, as illustrated in FIG. 3A. The valve is exemplified as a ball gravity valve, where the ball is pulled by gravity into the closed position, when the connector is oriented upside down. If the connector is oriented with the first section pointing upwards, as shown in FIG. 3A, the valve is configured to be open. If the first section is oriented downwards towards the ground, the valve will close. Thus, the third valve may be considered as a saftety valve for ensuring proper and efficient use.

In an embodiment of the disclosure, the device further comprises a third valve placed adjacent to an outlet of the first lumen.

Connector Attachment

To facilitate that the device is simply, easily, and quickly assembled from the kit of parts, the syringes are advantageously attached to the connector element by detachable fastening means, or detachably attached to the connector element by a locking mechanism. Examples of detachable fastening means include a screw, click-on, slide-on, or snap-fit mechanism.

In an embodiment of the disclosure, the syringes are detachably attached to the connector element by a locking mechanism, such as a screw, click-on, or slide-on, or snap-fit mechanism.

Further to facilitate simple, easy, and reliable attachment of the bioactive agent container, the attachment of the container is advantageously guided by a container receiver, as shown in FIG. 1A.

In an embodiment of the disclosure, the connector comprises a container receiver (3).

Further to facilitate simple, quick and reliable attachment of the bioactive agent container, the container advantageously has a sealed opening with a pierceable sealing. A sealed opening may be connected instantly by e.g. piercing or penetration. Thus advantageously, the seal is adapted to be pierced or penetrated. The sealed opening may be connected and pierced by a manual push towards the container receiver, as illustrated in FIGS. 1A and 2. Upon piercing the sealing, the connection to the container is created. The seal may be pierced by the first section of the connector element, which comprises a pointed end configured for penetrating the seal. Thus, the attachment is formed instantly, and the risk of spillage and wasted bioactive agent and other materials is reduced.

In an embodiment of the disclosure, the container has a sealed opening configured to be received at the first section of the connector. In a further embodiment, the seal adapted to be pierced. In a further embodiment, the first section of the connector comprises a pointed end configured for penetrating the sealed opening of the container. In a further embodiment, the pointed end has a needle shape.

Medical Paste

Advantageously, the device and kit according to the present disclosure is applied for producing and mixing a medical paste. By the term "medical paste" is meant a paste comprising a bioactive agent. An example of a bioactive agent is thrombin.

A "bioactive agent" is defined as any agent, drug, compound, composition of matter or mixture which provides some pharmacologic, often beneficial, effect that can be demonstrated in vivo or in vitro. An agent is thus considered bioactive if it has interaction with or effect on a cell tissue in the human or animal body. As used herein, this term further includes any physiologically or pharmacologically active substance that produces a localized or systemic effect in an individual. Bioactive agents may be a protein, such as an enzyme. Further examples of bioactive agents include, but are not limited to, agents comprising or consisting of an oligosaccharide, a polysaccharide, an optionally glycosylated peptide, an optionally glycosylated polypeptide, an oligonucleotide, a polynucleotide, a lipid, a fatty acid, a fatty acid ester and secondary metabolites. It may be used either prophylactically, therapeutically, in connection with treatment of an individual, such as a human or any other animal. The term "bioactive agent" as used herein does not encompass cells, such as eukaryotic or prokaryotic cells.

A "paste" according to the present disclosure has a malleable, putty-like consistency, such as toothpaste. A paste is a thick fluid mixture of pulverized solid/solid in powder form with a liquid. A paste is a substance that behaves as a solid until a sufficiently large load or stress is applied, at which point it flows like a fluid, i.e. a paste is flowable. Flowables conform efficiently to irregular surfaces upon application. Pastes typically consist of a suspension of granular material in a background fluid. The individual grains are jammed together like sand on a beach, forming a disordered, glassy or amorphous structure, and giving pastes their solid-like character. It is this "jamming together" that gives pastes some of their most unusual properties; this causes a paste to demonstrate properties of fragile matter. A paste is not a gel/jelly. A "slurry" is a fluid mixture of a powdered/pulverized solid with a liquid, such as water. Slurries behave in some ways like thick fluids, flowing under gravity and being capable of being pumped if not too thick. A slurry may functionally be regarded as a thin, watery paste, but a slurry generally contains more water than a paste. Substantially water-insoluble powder particles, such as cross-linked gelatine particles, will form a paste upon mixing with an aqueous medium.

A "gel" is a solid, jelly-like material that can have properties ranging from soft and weak to hard and tough. Gels are defined as a substantially dilute cross-linked system, which exhibits no flow when in the steady-state. By weight, gels are mostly liquid, yet they behave like solids due to a three-dimensional cross-linked network within the liquid. It is the crosslinks within the fluid that give a gel its structure (hardness) and contribute to stickiness (tack). In this way gels are a dispersion of molecules of a liquid within a solid in which the solid is the continuous phase and the liquid is the discontinuous phase. A gel is not a paste or slurry. For example, non-crosslinked gelatine is soluble and forms a gel upon contact with an aqueous medium such as water.

For a medical paste to be discharged from a syringe, it should be flowable, when subjected to a force applicable for a syringe. Thus, by the term "flowable paste" is meant a paste having a viscosity facilitating a steady flow, when subjected to a force applicable for a syringe. An example of a flowable paste is a paste having a viscosity between 500-3500 Pa·s, when measured at 30° C. and a relative humidity between 65-75%.

In an embodiment of the disclosure, the paste is flowable.

Forming a medical paste, such as a flowable medical paste, requires mixing of the bioactive agent with a paste or a paste forming material. Typically, bioactive agents are stored in a solid and dried state, such as a powdered form, facilitating stable storage of the active agent, and flexible concentrations by mixing the bioactive agent with a diluent in an adjustable ratio. Thus, for the bioactive agent to be administered by a syringe injection, the solid bioactive agent must first be reconstituted. Forming a medical paste therefore typically requires the steps of mixing a solid bioactive agent with a liquid or diluent to reconstitute the bioactive agent, and subsequently mixing the reconstituted bioactive agent with a paste forming material, which may also be referred to as "paste precursor".

By the term "paste forming material" is meant a material for forming a paste from a liquid phase, such as a reconstituted bioactive agent. Thus, a paste forming material may also be referred to as a precursor material for forming a paste.

The reconstituted bioactive agent is obtained by mixing the bioactive agent with a liquid with low viscosity, such as sterile water or saline water, thereby ensuring uniform reconstitution. Thus, the reconstituted bioactive agent is a liquid with low viscosity. A paste may be obtained from the reconstituted bioactive agent by adding a paste forming material, which inherently increases the viscosity.

Components

The present disclosure provides a simple, fast, easy, and convenient mixing of a liquid, a bioactive agent, and a paste forming material into a paste, such as a flowable paste. The efficiency of the resulting paste will depend on the type of components (i.e. liquid type, bioactive type, and paste forming material), the degree of mixing of the components and the distribution of the components within the paste, as well as the ratio between the components.

Bioactive Agent and Liquid

For the flowable paste to act as a haemostatic matrix, the bioactive agent is advantageously of a type, which acts as a clotting agent, such as thrombin.

Bioactive agents, such as thrombin, are typically expensive and stored in a solid and/or dried state to ensure chemical stability, longer storage times, and thus lower material waste. Advantageously the bioactive agent is a lyophilized agent, such as lyophilized thrombin. Lyophilization, is also known as freeze-drying, and involves dehydration of the bioactive agent, such that it is preserved and stored in a dried solid state. Thus, lyophilization provides an efficient storage form. However, for the lyophilized bioactive agent to be applied by injection, the lyophilized agent must be reconstituted by mixing with a liquid.

It is known in the art that the storage life of injectable substances, such as thrombin, is increased when the substance is stored in a powdered state. Lyophilization is one way of producing a powdered substance from a liquid based material. It involves a rapid freezing of the material at a very low temperature followed by a rapid dehydration by sublimation in a high vacuum.

The resulting lyophilized substance is typically stored in a glass vial or cartridge which is closed by a cap, such as a rubber stopper or septum. It is necessary to reconstitute the powdered or solid substance prior to administration. This is accomplished by mixing the powdered substance with a suitable diluent or liquid.

Further, to ensure sufficient uniform mixing of the bioactive agent within the paste, such that the paste acts as an efficient haemostatic matrix, the bioactive agent is advantageously reconstituted by a liquid capable of dissolving the agent or keeping the agent in essential stable suspension. Further advantageously, the liquid is of a type which acts as a diluent, such that the concentration of the bioactive agent can be easily adjusted. For example, thrombin may be easily dissolved and/or suspended by water, sterile water, saline water, sterile saline, or a mixture of water and glycerol.

In an embodiment of the disclosure, the bioactive agent is a dried or lyophilized substance. In a further embodiment, the bioactive agent comprises thrombin. In a further embodiment, the bioactive agent comprises or consists of lyophilized thrombin.

In one embodiment of the disclosure, the thrombin is recombinant thrombin.

In one embodiment of the disclosure, the thrombin is human thrombin.

In an embodiment of the disclosure, the liquid is a diluent. In a further embodiment, the liquid is an aqueous medium selected from the group of: water, glycerol, sterile water, saline, sterile saline, a calcium chloride solution, a buffered aqueous solution, and combinations thereof.

Thrombin is added to the paste of the present disclosure in an amount sufficient to ensure effective haemostasis of the paste. In one embodiment thrombin will be present at a concentration in the range of about 100 IU/ml paste to about 500 IU/ml paste, such as about 150 IU/ml paste to about 450 IU/ml paste, for example about 200 IU/ml paste to about 400 IU/ml paste, such as about 250 IU/ml paste to about 350 IU/ml paste.

In one embodiment, thrombin will be present in the paste at a concentration in the range of about 50 IU/g paste to about 5000 IU/g paste, preferably between about 100 IU/g paste to about 1000 IU/g paste, such as between about 200 IU/g paste to about 800 IU/g paste.

Reconstitution of a dry preparation of a bioactive agent such as thrombin is traditionally performed using a syringe with a needle to withdraw the diluent from one separate vial and inject it into another separate vial containing the dry thrombin, whereupon the latter vial is shaken or swirled to thoroughly mix the two constituents. The syringe with needle is then used to withdraw from this vial the desired amount of reconstituted bioactive agent. Because two separate containers are used, the person reconstituting the bioactive agent must be certain to mix the correct amounts such that a proper concentration of the mixture results.

In the present disclosure, the components are pre-loaded in the syringe and containers in predefined amounts and ratios. Thus, the steps of measuring the correct amount of the components are avoided, and a predefined amount of paste is rapidly, easily, and conveniently produced.

Paste Forming Material

To ensure the formation of an effective paste, such as a paste with sufficient flowability to be delivered to a target site by a syringe, and such that the delivered paste may be precisely and fixedly positioned at the target site, certain paste forming materials and certain paste compositions (i.e. ratios between the components) were found advantageous.

Advantageously, the paste forming material comprises a biocompatible polymer.

The biocompatible polymer of the present disclosure may be a biologic or a non-biologic polymer. Suitable biologic polymers include proteins, such as gelatine, collagen, albumin, hemoglobin, casein, fibrinogen, fibrin, fibronectin, elastin, keratin, and laminin; or derivatives or combinations thereof. Particularly preferred is the use of gelatine or collagen, more preferably gelatine. Other suitable biologic polymers include polysaccharides, such as glycosaminoglycans, starch derivatives, xylan, cellulose derivatives, hemicellulose derivatives, agarose, alginate, and chitosan; or derivatives or combinations thereof. Suitable non-biologic polymers will be selected to be degradable by either of two mechanisms, i.e. (1) break down of the polymeric backbone or (2) degradation of side chains which result in aqueous solubility. Exemplary nonbiologic polymers include synthetics, such as polyacrylates, polymethacrylates, polyacrylamides, polyvinyl resins, polylactide-glycolides, polycaprolactones, and polyoxyethylenes; or derivatives or combinations thereof. Also combinations of different kinds of polymers are possible.

In one embodiment, the biocompatible polymer is biologically absorbable. Examples of suitable biologically absorbable materials include gelatine, collagen, chitin, chitosan, alginate, cellulose, oxidised cellulose, polyglycolic acid, polyacetic acid and combinations thereof. It will be understood that various forms thereof, such as linear or cross-linked forms, salts, esters and the like are also contemplated for the present disclosure. In a preferred embodiment of the invention, the biologically absorbable material is gelatine. Gelatine is preferred since gelatine is highly biologically absorbable. Furthermore, gelatine is highly biocompatible, meaning that it is non-toxic to an animal, such as a human being, when/if entering the blood stream or being in long-term contact with human tissues.

The gelatine typically originates from a porcine source, but may originate from other animal sources, such as from bovine or fish sources. The gelatine may also be synthetically made, i.e. made by recombinant means.

In a preferred embodiment the biocompatible polymer is cross-linked. Cross-linking usually renders the polymer substantially insoluble in an aqueous medium. In one embodiment, the biocompatible polymer consists of powder particles which are substantially insoluble in an aqueous medium. Any suitable cross-linking methods known to a person of skill may be used including both chemical and physical cross-linking methods.

In an embodiment of the disclosure, the paste forming material comprises water-insoluble particles and/or cross-linked particles. In a further embodiment, the paste forming material comprises cross-linked gelatine particles.

The cross-linked powder particles are in one embodiment less than approximately 1000 microns in size, i.e. so that they are able to pass through a 1×1 mm sieve.

Generally at least 90% of the powder particles have a diameter of between 1 µm and 1200 µm.

In one embodiment, the average particle diameter is between 1 µm and 1000 µm, such as between 10 µm and 800 µm, for example between 50 µm and 600 µm, such as between 100 µm and 500 µm, for example between 200 µm and 400 µm, such as about 300 µm.

In some applications it is desirable to have a smaller particle size, whereby a smoother paste can be obtained. Thus in one embodiment, the average particle diameter is less than 100 µm, such as less than 50 µm, for example less than 30 µm, such as less than 20 µm, for example less than 10 µm. One example of an application where a smoother paste is desirable is in the control of bone bleeding.

Particles of a certain size distribution can be achieved by passing a powdered composition through one or more sieves having a certain mesh size and collecting the powder which passes through and/or is retained by a certain mesh size. For example, powder particles having a size distribution between approximately 200 µm and 1000 µm can be obtained by collecting the powder which is able to pass through a 1×1 mm sieve but is retained by a 0.2×0.2 mm sieve.

In one embodiment, the paste forming material comprises or consists of cross-linked gelatine particles obtained from a micronized porous gelatine sponge, which has been cross-linked by dry heat treatment.

The paste forming material is pre-loaded in the second syringe as illustrated in FIG. 1A, and upon mixing with the reconstituted bioactive agent, the paste is formed in the syringe as illustrated in FIG. 2.

To further facilitate fast formation of the paste, and fast and uniform mixing between the paste forming material and the reconstituted bioactive agent, it was found advantageously that the paste forming material is in the form of a solid, such as a dry composition, dried paste, or a powder. Further advantageously, the powder may be pressed powder, and shaped into a pellet. Pressed powders or pellets are easily pre-loaded into a syringe, and provides a fixed dosage. Thus, careful measurement of amounts of paste forming material is avoided. The paste forming material may also be provided as a vacuum expanded dry paste, having a density between about 1 mg/ml to about 40 mg/ml.

In an embodiment of the disclosure, the paste forming material is in the form of a solid, such as a dry composition. In a further embodiment, the paste forming material is a dried paste, such as a lyophilized paste. In another and further embodiment, the paste forming material is in the form of a powder, or pressed powder. In another embodiment, the paste forming material has a density between about 1 mg/ml to about 40 mg/ml, such as between 5 mg/ml to about 35 mg/ml, for example between about 10 mg/ml to about 35 mg/ml.

Advantageously, the components are pre-loaded in the syringe and containers in predefined amounts and ratios. Thus, measurements of components amounts are avoided, and a predefined amount or volume of paste is rapidly, easily, and conveniently produced.

In an embodiment of the disclosure, the volume of paste formed in the syringe is between 1-15 ml, more preferably between 6-12 ml, and most preferably between 7-10 ml, such as 8 ml.

It was found that the present disclosure may provide pastes that act as a haemostatic matrix, and further are especially efficient as haemostatic matrix due to the composition, flowability, and rheology.

In an embodiment of the disclosure, the paste is a haemostatic paste.

Items

The presently disclosed may be described in further detail with reference to the following items.

1. A device (1) for reconstituting a bioactive agent and forming a paste (10), the device comprising:
    a container (2) containing the bioactive agent,
    a first syringe (4) containing a liquid,
    a second syringe (5) containing a paste forming material,
    a connector element (6) configured for establishing sequential fluid connections between 1) the first syringe and the container, 2) the container and the second syringe, and 3) the first and second syringes, such that the liquid can be transferred from the first syringe to the container to reconstitute the bioactive agent, whereupon the reconstituted bioactive agent can be transferred from the container into the second syringe to form a paste, and the paste can be transferred to the first syringe.

2. The device according to item 1, wherein the connector element is adapted to have a first configuration providing simultaneous fluid passageway between the first syringe and the container, and the container and the second syringe, and a second configuration providing a fluid passageway between the first and second syringe.

3. The device according to any of the preceding items, wherein the connector element comprises at least two valves (7, 8) adapted to have a first arrangement providing simultaneous fluid passageway between the first syringe and the container, and the container and the second syringe, and a second arrangement providing a fluid passageway between the first and second syringe.

4. The device according to item 3, wherein at least the first valve (7) is adapted as a flow direction controller with two set points, such that it either provides a direct fluid passageway between the first syringe and the container, or a direct fluid passageway between first and second syringe.

5. The device according to item 4, wherein the device is adapted for providing a unidirectional fluid flow from the first syringe to the container, and from the container to the second syringe, when the first valve is in the first set point.

6. The device according to any of items 4-5, wherein the device is adapted for providing a bidirectional fluid flow from the second syringe to the first syringe and vice versa, when the first valve is in the second set point.

7. The device according to any of items 4-6, wherein the set point of the first valve is adapted to be controlled by a liquid pressure and/or gravity.
8. The device according to any of items 3-7, wherein the first valve is a one-way valve.
9. The device according to any of the preceding items, wherein the connector comprises a first section (6*a*) for fluidly attaching the container, a second section (6*b*) for fluidly attaching the first syringe, a third section (6*c*) for fluidly attaching the second syringe.
10. The device according to item 9, wherein the first section comprises two lumens (6*a*.1, 6*a*.2).
11. The device according to item 10, wherein the first valve (7) is configured for controlling the flow of the first lumen (6*a*.1), and the second valve is configured for controlling the flow of the second lumen (6*a*.2).
12. The device according to any of items 10-11, wherein the first lumen (6*a*.1) is configured for fluidly connecting the first syringe to the container, and the second lumen (6*a*.2) is configured for fluidly connecting the container to the second syringe, when first valve is in the first set point.
13. The device according to any of items 10-12, wherein the second valve is placed in the second lumen.
14. The device according to any of items 3-13, wherein the second valve is a one-way valve.
15. The device according to any of items 10-14, wherein the first valve is placed at a fluid inlet of the first lumen.
16. The device according to any of the preceding items, wherein the first, second, and third sections of the connector element form an inverse T-shape, i.e. ⊥.
17. The device according to any of the preceding items, comprising a third valve placed adjacent to an outlet of the first lumen.
18. The device according to any of the preceding items, wherein the paste forming material comprises a biocompatible polymer.
19. The device according to any of the preceding items, wherein the paste forming material comprises water-insoluble particles and/or cross-linked particles.
20. The device according to any of the preceding items, wherein the paste forming material comprises cross-linked gelatine particles.
21. The device according to any of the preceding items, wherein the paste forming material is in the form of a solid, such as a dry composition.
22. The device according to any of the preceding items, wherein the paste forming material is a dried paste, such as a lyophilized paste.
23. The device according to any of the preceding items, wherein the paste forming material is in the form of a powder, or pressed powder.
24. The device according to any of the preceding items, wherein the paste forming material has a density between about 1 mg/ml to about 40 mg/ml, such as between 5 mg/ml to about 35 mg/ml, for example between about 10 mg/ml to about 35 mg/ml.
25. The device according to any of the preceding items, wherein the bioactive agent is a dried or lyophilized substance.
26. The device according to any of the preceding items, wherein the bioactive agent comprises thrombin.
27. The device according to any of the preceding items, wherein the bioactive agent comprises or consists of lyophilized thrombin.
28. The device according to any of the preceding items, wherein the liquid is a diluent.
29. The device according to any of the preceding items, wherein the liquid is an aqueous medium selected from the group of: water, glycerol, sterile water, saline, sterile saline, a calcium chloride solution, a buffered aqueous solution, and combinations thereof.
30. The device according to any of the preceding items, wherein the paste is a haemostatic paste.
31. The device according to any of the preceding items, wherein the paste is flowable.
32. The device according to any of the preceding items, wherein the volume of paste formed in the syringe is between 1-15 ml, more preferably between 6-12 ml, and most preferably between 7-10 ml, such as 8 ml.
33. The device according to any of the preceding items, wherein the syringes are detachably attached to the connector element by a locking mechanism, such as a screw, click-on, slide-on, or snap-fit locking mechanism.
34. The device according to any of the preceding items, wherein the connector element comprises a container receiver (3).
35. The device according to any of the preceding items, wherein the container has a sealed opening configured to be received at the first section of the connector element.
36. The device according to item 35, wherein the seal is adapted to be pierced.
37. The device according to any of items 9-36, wherein the first section of the connector element comprises a pointed end configured for penetrating the sealed opening of the container.
38. The device according to item 37, wherein the pointed end has a needle shape.
39. A kit of parts for the device according to any of items 1-38, comprising a container containing a bioactive agent, a first syringe containing a liquid, a second syringe containing a paste forming material, and a connector element.
40. A method for reconstituting a bioactive agent and forming a paste, the method comprising:
    a) providing a first syringe containing a liquid, a container containing a bioactive agent, a second syringe containing a paste forming material, and a connector element configured for establishing sequential fluid connections between 1) the first syringe and the container, 2) the container and the second syringe, and 3) the first and second syringes,
    b) attaching the first syringe, the container, the second syringe to the connector element,
    c) pushing the piston of the first syringe, whereby the liquid is transferred from the first syringe to the container to reconstitute the bioactive agent, and consecutively the reconstituted bioactive agent is transferred from the container into the second syringe to form a paste,
    d) mixing the paste by alternately pushing the piston of the second syringe and the first syringe, such that the paste is transferred between the second and first syringes.
41. The method according to item 40, wherein the mixing of step (d) is obtained by pushing the pistons at least 6 times.
42. The method according to any of items 40-41, configured to be carried out using the device according to any of items 1-37 or the kit according to item 38.

43. Use of the device according to any of items 1-38 or the kit according to item 98 for the method according to any of items 40-41.

REFERENCE NUMBERS

1—device
2—container for bioactive agent
3—container receiver
4—first syringe
4a—first syringe needle
5—second syringe
5a—second syringe needle
6—connector element
6a—connector first section
6a.1—first lumen
6a.2—second lumen
6b—connector second section
6c—connector third section
7—first valve
8—second valve
9—third valve
10—paste

The invention claimed is:

1. A device for reconstituting a bioactive agent and forming a paste, the device comprising:
   a container containing the bioactive agent,
   a first syringe containing a liquid,
   a second syringe containing a paste forming material, and
   a connector element configured for establishing sequential fluid connections between
   1) the first syringe and the container, 2) the container and the second syringe, and 3) the first syringe and the second syringe, such that the liquid can be transferred from the first syringe to the container to reconstitute the bioactive agent,
   whereupon the reconstituted bioactive agent can be transferred from the container into the second syringe to form a paste, and the paste can be transferred to the first syringe, and wherein the connector element comprises at least a first valve and a second valve adapted to have a first arrangement providing simultaneous fluid passageway between the first syringe and the container, and the container and the second syringe, and a second arrangement providing a fluid passageway between the first syringe and the second syringe.

2. The device according to claim 1, wherein at least the first valve is adapted as a flow direction controller with a first set point and a second set point, such that the flow direction controller either provides a direct fluid passageway between the first syringe and the container, or a direct fluid passageway between the first syringe and the second syringe.

3. The device according to claim 2, wherein the device is adapted for providing a unidirectional fluid flow from the first syringe to the container, and from the container to the second syringe, when the first valve is in the first set point.

4. The device according to claim 2, wherein the device is adapted for providing a bidirectional fluid flow from the second syringe to the first syringe and vice versa, when the first valve is in the second set point.

5. The device according to claim 2, wherein the first set point of the first valve is adapted to be controlled by a liquid pressure and/or gravity.

6. The device according to claim 1, wherein the connector comprises a first section-for fluidly attaching the container, a second section for fluidly attaching the first syringe, and a third section for fluidly attaching the second syringe.

7. The device according to claim 6, wherein the first section comprises a first lumen and a second lumen.

8. The device according to claim 7, wherein the first valve is configured for controlling a flow of the first lumen, and the second valve is configured for controlling a flow of the second lumen.

9. The device according to claim 7, wherein the second valve is placed in the second lumen.

10. The device according to claim 7, wherein the first valve is placed at a fluid inlet of the first lumen.

11. The device according to claim 6, wherein the first, second, and third sections of the connector element form an inverse T-shape, i.e. ⊥.

12. The device according to claim 1, wherein the paste forming material comprises a biocompatible polymer.

13. The device according to claim 1, wherein the bioactive agent is a dried or lyophilized substance.

14. The device according to claim 1, wherein the paste is a haemostatic paste.

15. The device according to claim 1, wherein the first valve is a one-way valve.

16. The device according to claim 1, wherein the second valve is a one-way valve.

17. The device according to claim 1, wherein the liquid is a diluent.

18. A kit of parts for the device according to claim 1, comprising the container containing the bioactive agent, the first syringe containing the liquid, the second syringe containing the paste forming material, and the connector element.

19. A method for reconstituting a bioactive agent and forming a paste, the method comprising:
   a) providing a first syringe with a first piston, the first syringe containing a liquid, a container containing a bioactive agent, a second syringe with a second piston, the second syringe containing a paste forming material, and a connector element configured for establishing sequential fluid connections between 1) the first syringe and the container, 2) the container and the second syringe, and 3) the first syringe and the second syringe;
   b) attaching the first syringe, the container, the second syringe to the connector element;
   c) pushing the first piston of the first syringe, whereby the liquid is transferred from the first syringe to the container to reconstitute the bioactive agent, and consecutively the reconstituted bioactive agent is transferred from the container into the second syringe to form a paste; and
   d) mixing the paste by alternately pushing the second piston of the second syringe and the first piston of the first syringe, such that the paste is transferred between the second syringe and first syringe.

20. The method according to claim 19, wherein the mixing in (d) is performed by pushing the first piston and the second piston at least 6 times.

* * * * *